United States Patent [19]

Green et al.

[11] 4,070,455

[45] Jan. 24, 1978

[54] PROCESS FOR PREPARING INJECTABLE DESENSITIZING COMPOSITIONS AND PRODUCTS THEREOF IN MICROPARTICLE FORM

[75] Inventors: Geoffrey Green, Worthing; Brian George Overell, Dorking; Anthony Phillip Hart, Worthing, all of England

[73] Assignee: Beecham Group Limited, England

[21] Appl. No.: 729,489

[22] Filed: Oct. 4, 1976

Related U.S. Application Data

[63] Continuation-in-part of Ser. No. 548,701, Feb. 10, 1975, abandoned.

[30] Foreign Application Priority Data

Feb. 16, 1974 United Kingdom ............... 7156/74

[51] Int. Cl.² ...................... A61K 27/14; C07G 7/00
[52] U.S. Cl. .................................................. 424/91
[58] Field of Search ........................................ 424/91

[56] References Cited

U.S. PATENT DOCUMENTS

| | | | |
|---|---|---|---|
| 3,541,201 | 11/1970 | Brown | 424/91 X |
| 3,761,585 | 9/1973 | Mullan et al. | 424/91 |
| 3,792,159 | 2/1974 | Green et al. | 424/91 |
| 3,794,630 | 2/1974 | Mullan et al. | 260/112 R |

*Primary Examiner*—Shep K. Rose
*Attorney, Agent, or Firm*—Jacobs & Jacobs

[57] ABSTRACT

Finely divided micro-particles of tyrosine having a glutaraldehyde-treated allergen dispersed therein are prepared by mixing a solution of tyrosine in a strong aqueous acid with a solution of glutaraldehyde-treated ragweed pollen extract as the allergen and then neutralizing the resultant solution.

10 Claims, No Drawings

PROCESS FOR PREPARING INJECTABLE DESENSITIZING COMPOSITIONS AND PRODUCTS THEREOF IN MICROPARTICLE FORM

CROSS-REFERENCE TO RELATED APPLICATION

This application is a continuation-in-part application of application Ser. No. 548,701 which was filed on Feb. 10, 1975, now abandoned.

BACKGROUND OF THE INVENTION

This invention relates to a process for preparing finely divided micro-particles of tyrosine having a water-soluble glutaraldehyde-treated ragweed pollen extract as allergen dispersed therein for use in desensitisation therapy of persons who are liable to allergic reactions and the product thereof.

U.S. Pat. No. 3,792,159 describes a process for preparing injectable compositions for use in desensitisation therapy which consist of finely-divided micro-particles of tyrosine having an allergen dispersed therein, which process comprises mixing a solution of tyrosine in a strong aqueous acid with an aqueous or water-miscible solution of the desired allergen and simultaneously or subsequently neutralising the resultant solution whereby finely-divided micro-particles of tyrosine containing the allergen are precipitated; and subsequently separating the said micro-particles. The Patent refers quite generally to allergens and relates to a valuable method of preparing tyrosine micro-particles containing such allergens. The process conditions are such that the process is effective only with water-soluble allergens and several examples of such allergens are described.

U.S. Pat. No. 3,541,201 describes the preparation of finely divided micro-particles of tyrosine having allergens dispersed therein. It is believed clear from this Patent that the allergens must be water soluble.

U.S. Pat. No. 3,794,630 and its divisional U.S. Pat. No. 3,761,585 describe the preparation and use for desensitization therapy of a particular class of allergens not mentioned or suggested in the aforesaid U.S. Pat. Nos. 3,792,159 and 3,541,201, namely allergens that have been modified by treatment inter alia with glutaraldehyde. These modified allergens probably contain intra-molecular cross-linking with possibly some inter-molecular cross-linking and have reduced allergenicity relative to the unmodified allergen. In order to obtain a modified product of the desired utility it is recommended in U.S. Pat. Nos. 3,794,630 and 3,761,585 that the modification process is carried out under conditions which yield a water-insoluble or sparingly water-soluble modified allergen, and only modified allergens of such solubility are specifically described. For injection, it is disclosed in these Patents that the modified allergens can be formulated with adjuvants such as tyrosine, and examples of such formulation with water-insoluble and sparingly water-soluble modified allergens are given.

It is believed that the skilled reader of U.S. Pat. Nos. 3,794,630 and 3,761,585 attempting to prepare a product having the desired utility disclosed therein would follow the recommendations in the Patents and would adjust the modification process to give water-insoluble or sparingly water-soluble modified allergens. It is similarly believed that any formulation with adjuvants would be carried out with modified allergens of this solubility. As would therefore be expected, there is no specific disclosure in the Patents of the preparation of a water soluble modified allergen, nor is there any disclosure or recommendation in the Patents of the formulation of a water-soluble modified allergen with an adjuvant. It is further believed that the skilled reader of U.S. Pat. Nos. 3,792,159 and 3,541,201 would not consider using the modified allergens of U.S. Pat. Nos. 3,794,630 and 3,761,585 in the process and formulations described therein, as for such use the modified allergens would have to be water soluble while the modified allergens recommended in U.S. Pat. Nos. 3,794,630 and 3,761,585 as having the desired utility are water insoluble or sparingly water-soluble. Adjustment of the modification process described in U.S. Pat. Nos. 3,794,630 and 3,761,585 to give water soluble modified allergens would be going directly against the teaching therein, and would result in a product for which no utility predictions could be made from these Patents.

It has now surprisingly been discovered that water soluble glutaraldehyde modified ragweed pollen extract may be used in the process of U.S. Pat. No. 3,792,159 to give a product which advantageously combines efficacy with safety in desensitization therapy.

DESCRIPTION OF THE INVENTION

The present invention provides a process for preparing finely-divided micro-particles of tyrsoine having a glutaraldehyde-treated ragweed pollen extract as allergen dispersed therein, which process comprises mixing (a) an aqueous solution of a water-soluble glutaraldehyde modified allergenic ragweed pollen extract of a whole allergen with (b) a solution of tyrosine in a strong aqueous acid; and simultaneously or subsequently neutralizing such mixture of solutions, thereby precipitating the required finely-divided micro-particles of tyrosine containing a glutaraldehyde-treted ragweed pollen as an extract of the whole allergen dispersed therein.

The solution of the thus modified ragweed pollen used in this process may either be obtained directly by reacting an aqueous solution of whole ragweed pollen with glutaraldehyde under substantially neutral conditions or by making up a solution of a dried modified ragweed pollen previously prepared by such a process.

The allergenic material for present use is an extract of an allergen such as, for example, and extract of one or more pollens or of house dust or of the house dust mites, *Dermatophagoides pteronyseinus*, which breed in house dust, or of moulds or animal hair, dander or fur. The extract may be prepared by any of the conventional ways for preparing allergen extracts and, if desired, the allergen material so extracted may be purified by precipitation, dialysis or gel filtration.

The allergenic extract of whole allergen is modified by treatment with glutaraldehyde at pH 7 ± 1. A solution of the water-soluble glutaraldehyde treated allergenic extract of whole allergen at pH 7 ± 1, obtained either as the reaction mixture from the modification process or from the solvation of solid modified allergenic extracts of whole allergen, is then mixed with a solution of tyrosine in a strong aqueous acid. This step is carried out as described in U.S. Pat. No. 3,792,159 and the strong acid is usually an inorganic acid, preferably hydrochloric acid.

The resulting mixture of solutions of modified allergen and tyrosine is neutralised as described in the parent patent. By neutralisation is means an adjustment of pH to a value within the range 4.0 to 7.5. This neutalisation can be carried out subsequently to the mixing of the two aforesaid solutions. However, it is important that, at no time, or at least at no prolonged time, during the neutralisation does the pH of the solution rise appreciably above 7.5. This condition can be met by vigorous stirring of the solution and by the use only of the required amount of base, if desired. Various buffering agents can usefully be added to the solutions of modified allergen to assist in pH control during the mixing and neutralisation stages.

A particularly useful method of carrying out the neutralisation is for separate streams of the solution of tyrosine in acid and the neutralising base to be run into the solution of modified allergen, the rates of flow of the added solutions being controlled by pH-stat, that is by equipment which regulates the flow of one or both of the solutions so that the pH of the reaction mixture remains substantially constant at a predetermined level. We have found that optimum results are usually obtained by pH control with in the range 6.5 to 7.5 though the precise pH varies according to the nature of the allergen.

The result of the neutralisation is the immediate precipitation of the tyrosine as microfine particles within which the solution of modified allergen is occluded and/or adsorbed. After the precipitation the mixture is either washed immediately or allowed to stand for a period of from a few phenol-saline, to a day or two prior to washing. Desirably the precipitate is obtained as fine as possible and this is achieved by rapid neutralisation of the solution coupled with vigorous agitation while this is being carried out.

As described in U.S. Pat. No. 3,792,159 the resulting precipitate of micro-fine particles of tyrosine containing the modified allergen may be removed from the solution by centrifugation or filtration and washed, e.g. with henol-saline, before being resuspended in a physiologically-acceptable carrier such as phenol-saline, or sterile water, to produce an injectable composition suitable for use in desensitisation therapy.

The materials produced by the process of this invention are believed to be novel, and as such form part of the invention.

Accordingly, the present invention also provides finely-divided micro-particles of tyrosine having a water-soluble glutaraldehyde treated allergen dispersed therein.

Suitably the allergen is an extract of one or more pollens. The allergen may also with advantage be an extract of house dust or house dust mites.

The following Examples illustrate the present invention:

EXAMPLE 1

14 mls. of a neutral solution of approximately 2 mgm/ml dry weight of grass pollen extract which had been partially purified by dialysis or fractionation was chemically modified by the addition of an equal volume of 0.25% w/v purified glutaraldehyde and the mixture stirred for a period of approximately 2 hours. To the above mixture was added 10 mls of a phosphate buffer solution pH 7 ± 1, followed by the simultaneous addition of 10 mls of L-tyrosine (prepared by dissolving 24 gm. L-tyrosine to 100 mls in 3.8 N hydrochloric acid) and 10 mls of 3.2 N sodium hydroxide, with vigorous agitation at pH 7 ± 1. The suspension so formed was centrifuged, washed repeatedly with buffered saline to remove contaminants and resuspended in buffered phenol saline pH 6 ± 1 to a volume of 60 mls.

EXAMPLE 2

Tyrosine having modified Bermuda grass pollen dispersed therein.

14 mls of a neutral solution of 10% w/v Bermuda grass pollen extract which had been partially purified by dialysis or fractionation was chemically modified by the addition of an equal volume of 1% w/v purified glutaraldehyde and the mixture stirred for a period of approximately 2 hours. Unreacted glutaraldehyde was removed by dialysis.

To the fluid retentate was added 10 mls of a buffer solution of pH 7 ± 1, followed by the simultaneous addition of 10 mls of L-tyrosine (prepared by dissolving 24 gms of L-tyrosine to 100 mls in 3.8 N hydrochloric acid) and 10 mls of 3.2 N sodium hydroxide with vigorous agitation at pH 7 ± 1. The suspension so formed was centrifuged, washed repeatedly with buffered saline to remove contaminants and resuspended in buffered saline pH 6 ± 1 to a volume of 60 mls.

EXAMPLE 3

Tyrosine having modified cultivated rye pollen dispersed therein.

The process as described in Example 2 was repeated but as allergen there was used a 10% cultivated rye pollen extract.

EXAMPLE 4

Tyrosine having modified tree pollen dispersed therein.

The process as described in Example 2 was repeated but as allergen there was used a 10% w/v tree pollen extract.

EXAMPLE 5

Tyrosine having modified grass pollen dispersed therein.

A process as described in Example 2, but as allergen there was used a 10% grass pollen extract.

EXAMPLE 6

Tyrosine having modified short ragweed pollen dispersed therein.

A process as described in Example 2 but as allergen there was used a 6% short ragweed pollen extract and the purified glutaraldehyde was 0.6% w/v.

EXAMPLE 7

Tyrosine having modified D.pteronyssinus of dispersed therein.

12 mls. of a neutral solution of 10% D.pteronyssinus extract which had been partially purified by dialysis or fractionation was chemically modified by the addition of an equal volume of 4% w/v purified glutaraldehyde and the mixture stirred for a period of approximately 2 hours. Unreacted glutaraldehyde was removed by dialysis.

To the fluid retentate was added 10 mls. of a buffer solution of pH 7 ± 1, followed by the simultaneous addition of 10 mls. of L-tyrosine (prepared by dissolving 24 gm. of L-tyrosine to 100 mls. in 3.8 N hydrochloric acid) and 10 mls. of 3.2 N sodium hydroxide, with vigorous agitation at 7 ± 1.

The suspension so formed was centrifuged, washed repeatedly with buffered saline to remove contaminants and resuspended in buffered saling pH 6 ± 1 to a volume of 60 mls.

The products of Examples 1 to 7 are pharmaceutically acceptable and are suitable for use in desensitisation therapy as injectable compositions.

We claim:

1. A process of preparing finely-divided micro-particles of tyrosine having a water-soluble, glutaraldehyde-treated extract of ragweed pollen as allergen dispersed therein, which process comprises: mixing (a) an aqueous solution of a water-soluble glutaraldehyde-modified ragweed pollen extract with (b) a solution of tyrosine in a strong aqueous acid, and neutralising such mixture of solutions, thereby precipitating the required finely-divided micro-particles of tyrosine containing a water-soluble, glutaraldehyde-treated ragweed pollen extract dispersed therein.

2. A process according to claim 1 wherein the aqueous solution of modified ragweed pollen is obtained directly by reacting an aqueous solution of whole ragweed pollen with glutaraldehyde under substantially neutral conditions.

3. A pharmaceutical composition which can be injected, which composition comprises an anti-allergy effective amount of the material of claim 10 together with a pharmaceutically acceptable carrier.

4. A process according to claim 1, wherein the strong aqueous acid employed in stage (b) is hydrochloric acid.

5. A process according toclaim 1, wherein sodium hydroxide is employed to neutralise the reaction mixture.

6. A process according to claim 1, wherein a buffer is added to the reaction mixture before the neutralisation procedure is carried out.

7. A process according to claim 1, wherein the neutralising base and the solution of tyrosine in acid are run into the solution of modified ragweed pollen extract simultaneously.

8. A process according to claim 7, which is carried out at substantially constant pH by regulation of the rates of simultaneous addition of the solution of tyrosine and neutralising solution to the solution of modified ragweed pollen extract.

9. A process according to claim 1, wherein the mixture of solutions is neutralised after mixing.

10. Finely-divided micro-particles of tyrosine having a water soluble glutaraldehyde-treated ragweed pollen extract dispersed therein.

* * * * *